US 7,567,833 B2

(12) United States Patent
Moctezuma De La Barrera et al.

(10) Patent No.: US 7,567,833 B2
(45) Date of Patent: Jul. 28, 2009

(54) ENHANCED ILLUMINATION DEVICE AND METHOD

(75) Inventors: José Luis Moctezuma De La Barrera, Freiburg (DE); Harald Hoppe, Achern (DE)

(73) Assignee: Stryker Leibinger GmbH & Co. KG, Freiburg (DE)

(*) Notice: Subject to any disclaimer, the term of this patent is extended or adjusted under 35 U.S.C. 154(b) by 1233 days.

(21) Appl. No.: 10/795,844

(22) Filed: Mar. 8, 2004

(65) Prior Publication Data

US 2005/0195587 A1 Sep. 8, 2005

(51) Int. Cl.
*A61B 5/05* (2006.01)
*A61B 18/00* (2006.01)

(52) U.S. Cl. .............. 600/424; 600/407; 600/476; 362/572

(58) Field of Classification Search .............. 600/300, 600/407, 476; 362/572
See application file for complete search history.

(56) References Cited

U.S. PATENT DOCUMENTS

| | | | | |
|---|---|---|---|---|
| 3,360,640 A | 12/1967 | Seitz et al. | .......... | 240/1.4 |
| 3,891,842 A | 6/1975 | Strusinski | .......... | 240/1.4 |
| 5,159,361 A * | 10/1992 | Cambier et al. | .......... | 351/212 |
| 5,192,946 A | 3/1993 | Thompson et al. | .......... | 340/794 |
| 5,347,431 A | 9/1994 | Blackwell et al. | .......... | 362/11 |
| 5,424,913 A * | 6/1995 | Swindler | .......... | 361/687 |
| 5,526,812 A * | 6/1996 | Dumoulin et al. | .......... | 600/407 |
| 5,658,063 A | 8/1997 | Nasserbakht | .......... | 353/122 |
| 5,715,836 A | 2/1998 | Kliegis et al. | .......... | 128/898 |
| 5,769,078 A | 6/1998 | Kliegis | .......... | 128/653.11 |
| 5,772,593 A * | 6/1998 | Hakamata | .......... | 600/407 |
| 5,792,147 A | 8/1998 | Evans et al. | .......... | 606/130 |
| 5,803,905 A | 9/1998 | Allred et al. | .......... | 600/249 |
| 5,808,680 A | 9/1998 | Steckhan | .......... | 348/370 |
| 5,871,445 A | 2/1999 | Bucholz | .......... | 600/407 |
| 5,891,034 A | 4/1999 | Bucholz | .......... | 600/426 |
| 6,038,467 A | 3/2000 | De Bliek et al. | .......... | 600/424 |
| 6,076,008 A | 6/2000 | Bucholz | .......... | 600/427 |
| 6,160,582 A | 12/2000 | Hill | .......... | 348/370 |

(Continued)

FOREIGN PATENT DOCUMENTS

EP 0 421 130 A2 4/1991

(Continued)

OTHER PUBLICATIONS

Hoppe et al. "A New, Accurate and Easy to Implement Camera and Video Projector Model", *Studies in Health Technology and Informatics, Medicine Meets Virtual Reality (MMVR)*, (ISO Press) (pp. 204-206) (2002).

(Continued)

*Primary Examiner*—Eric F Winakur
*Assistant Examiner*—Helene Bor
(74) *Attorney, Agent, or Firm*—McCracken & Frank LLP

(57) ABSTRACT

A light source illuminates a field of interest that includes an illumination module capable of projecting illumination light to the field of interest and a light projector associated with the illumination module. The light source also includes an input device associated with the light projector; the input device capable of sending signals to the light projector such that the light projector simultaneously projects data light along with the illumination light to the field of interest.

62 Claims, 9 Drawing Sheets

U.S. PATENT DOCUMENTS

| | | |
|---|---|---|
| 6,246,900 B1 | 6/2001 | Cosman et al. ............. 600/426 |
| 6,290,645 B1 | 9/2001 | Goldfarb et al. ............ 600/249 |
| 6,309,345 B1 | 10/2001 | Stelzer et al. ............... 600/106 |
| 6,314,311 B1 * | 11/2001 | Williams et al. ............ 600/425 |
| 6,317,134 B1 | 11/2001 | Hagemark et al. .......... 345/512 |
| 6,374,135 B1 | 4/2002 | Bucholz ...................... 600/427 |
| 6,621,491 B1 | 9/2003 | Baumrind et al. ........... 345/419 |
| 6,690,964 B2 * | 2/2004 | Bieger et al. ................ 600/424 |
| 6,693,691 B2 | 2/2004 | Sato et al. .................... 349/113 |
| 6,694,164 B2 | 2/2004 | Glossop ....................... 600/407 |
| 6,697,761 B2 | 2/2004 | Akatsuka et al. ............ 702/151 |
| 2002/0077543 A1 | 6/2002 | Grzeszczuk et al. ......... 600/424 |
| 2002/0087075 A1 | 7/2002 | Bucholz ...................... 600/429 |
| 2003/0164953 A1 | 9/2003 | Bauch et al. ................. 356/611 |

FOREIGN PATENT DOCUMENTS

| | | |
|---|---|---|
| EP | 0 793 945 A1 | 10/1997 |
| WO | WO 94/19758 | 9/1994 |
| WO | WO 99/27839 | 6/1999 |
| WO | WO 01/05161 A1 | 1/2001 |

OTHER PUBLICATIONS

Heinz Wörn and Harold Hoppe "Augmented Reality in the Operating Theatre of the Future" (2002).

Hoppe et al. "Projector-based visualization for intraoperative navigation: first clinical results" *Proceedings of the 17th International Congress and exhibition on Computer Assisted Radiology and Surgery(CARS)* p. 771 (2003).

* cited by examiner

ENHANCED ILLUMINATION DEVICE AND METHOD

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

This invention relates to enhanced illumination devices and more particularly to operating room lighting systems and methods that additionally project data to assist the surgical team.

2. Description of the Background of the Invention

Proper illumination of a surgical site is very important to a successful surgical outcome. As such, the operating room light is typically position to provide high quality lighting without shadows to the surgical site. Operating room lights are mounted so that they can be positioned to provide good line of sight lighting to the operating field. Because of the favored position of the operating room light, there have been proposals to incorporate other systems used during surgery that rely on or require good line of sight into or attached to the operating room light. For instance, U.S. Patent Publication No. 2003/0164953 discloses attaching a tracking camera system to an operating room light.

In addition, it is desirable to provide enhanced augmented reality data to a field of interest, preferably to a surgical field. The incorporation of augmented reality into a surgical operating room lighting system will enable the surgical team to concentrate on the surgical site without the need to look away to an external display device to monitor the patient's data, to review information, or to use surgical navigation systems. There have been proposals to project data onto a surgical site however none of these proposals suggest using light from the operating room or a similar light source to project the data onto the patient.

SUMMARY OF THE INVENTION

One aspect of the present invention comprises a light source to illuminate a field of interest that includes an illumination module capable of projecting illumination light to the field of interest and a light projector associated with the illumination module. The light source also includes an input device associated with the light projector; the input device capable of sending signals to the light projector such that the light projector simultaneously projects data light along with the illumination light to the field of interest.

An additional aspect of the present invention comprises a method of providing light to a field of interest that comprises the steps of projecting illumination light from an illumination module; projecting data from a light projection module associated with the illumination module; and capturing surface data from within the field of interest.

A still further aspect of the present invention includes a light source to illuminate a field of interest that comprises an illumination module comprising a series of digital light projectors capable of projecting illumination light to the field of interest. Also, the light source includes an input device associated with the illumination module; the input device capable of sending signals to the illumination module such that the illumination module simultaneously projects data light along with the illumination light to the field of interest.

DETAILED DESCRIPTION OF THE DRAWINGS

Figure 1:
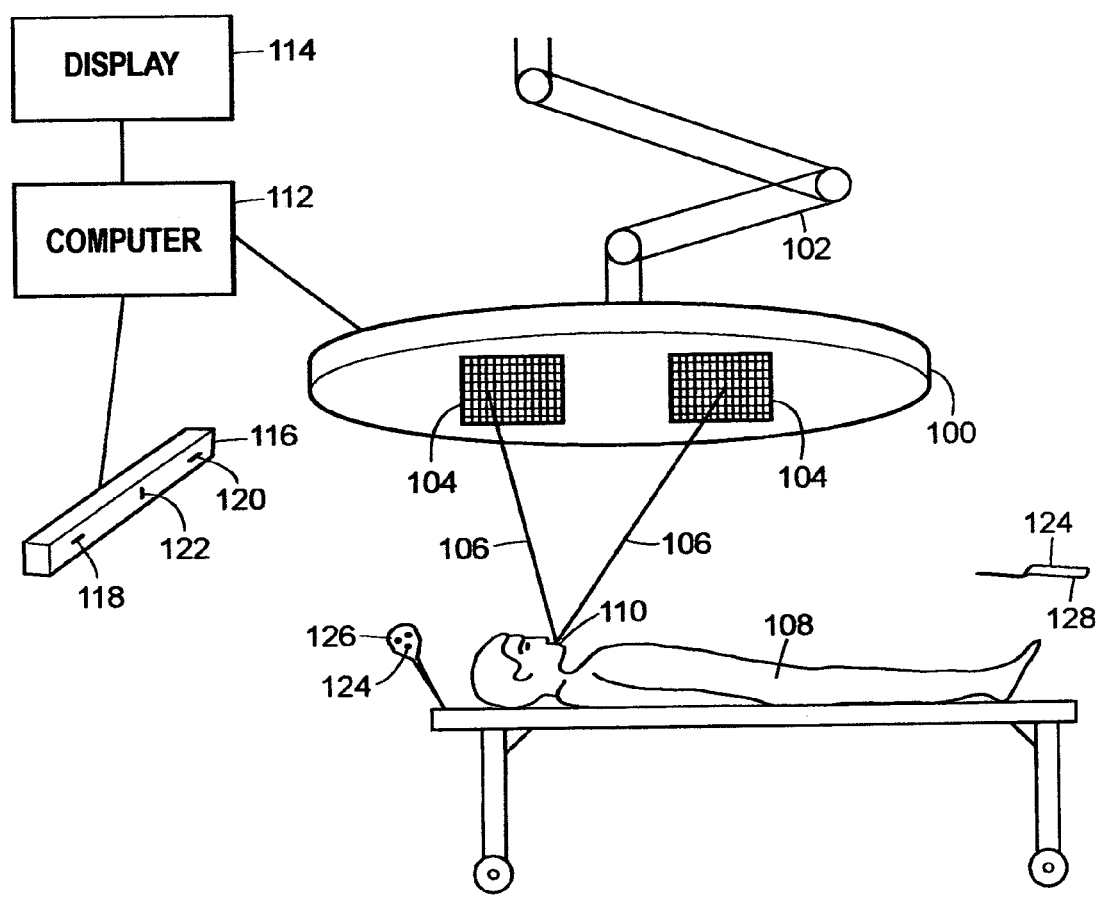
FIG. 1 is a schematic view of one embodiment of the present invention.

With reference to FIG. 1, a room light 100 is suspended using a movable support system 102. The room light 100 has light projection areas 104. Even though two light projection areas 104 are shown in FIG. 1, it is possible for some embodiments that a single light projection area 104 can be used while in other embodiments three or more light projection areas 104 will be used. The exact number of light projection areas 104 will depend on the amount of light needed and also the complexity of the data to be projected. The light projection areas 104 are capable of projecting both illumination light and data light. In one embodiment, the light projection areas 104 can be any type of system that is capable of projecting both ambient light and also data light at the same time. These systems include but are not limited to liquid crystal display projection systems (LCDP), such as those disclosed in U.S. Pat. No. 6,693,691, the disclosure of which is hereby incorporated by reference, and digital light projection systems (DLP), such as those disclosed in U.S. Pat. No. 5,658,063, the disclosure of which is hereby incorporated by reference. Both these systems are well known to those of skill in the technology of data and light projection. In other embodiments, the illumination light and the data light will be projected from different specialized light projection areas 104.

Depending on the technology used, each light projection area 104 can be made up of a series of light projection areas arranged in a matrix or can be a single lens that can project both the illumination light and the data light. In a surgical environment, the combined light projection areas 104 should project sufficient light to adequately illuminate the field of interest. In order to be sufficiently visible, the data light must be brighter than the illumination light. Light 106 is projected from the light projection areas 104 onto a patient 108. Typically the light 106 is projected onto the skin 110, bone or tissue of the patient 108. Because the relationship between the light projection areas and patient is not known and the currently visible surface of the patient is not flat, it will be necessary to calibrate the light 106. This can be done using conventional photogrammetry techniques well known to those in the art or by any other means of capturing the projection surface as surface extraction from 3D scanning, laser range scanning, etc and implicit or explicit registration techniques. One such technique involves the use of patterns of light and dark areas that can be placed in the field of interest. Based on the projection surface information, the projected light can be modified so that the display on the patient 108 appears clear and undistorted.

Figure 9:
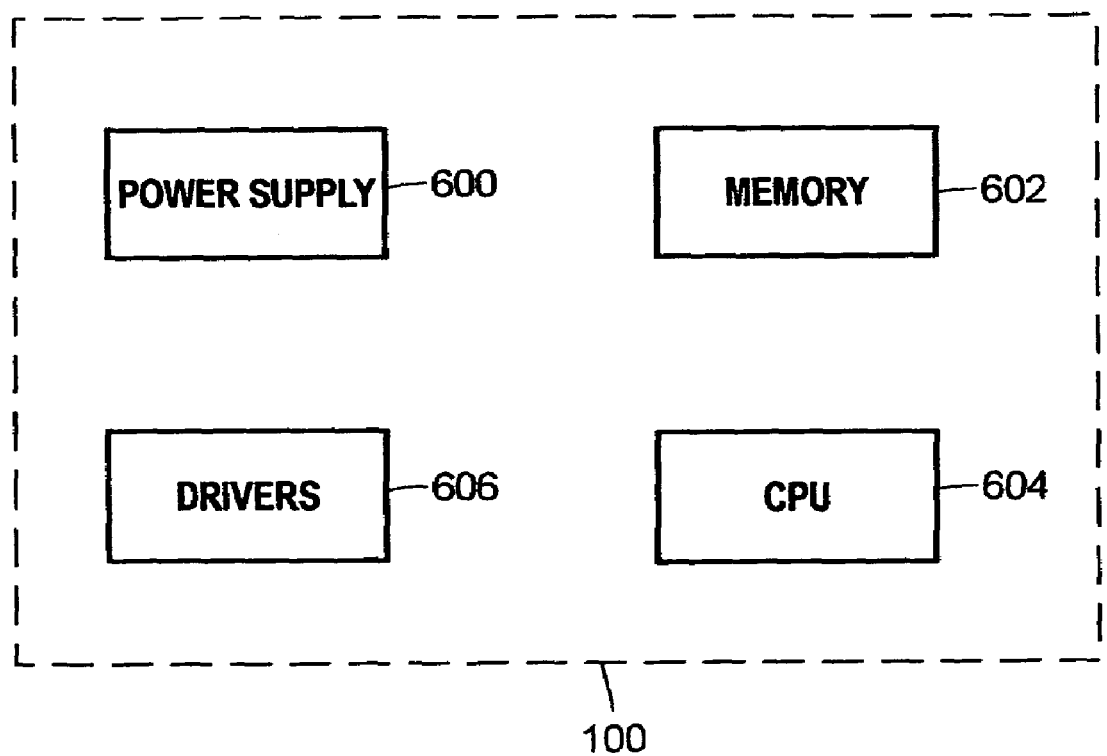
FIG. 9 is a schematic illustration of the interior of one embodiment of the light of the present invention.

FIG. 9 shows a schematic illustration of the internal structure of one embodiment of the room light 100. The room light 100 can include a power supply 600, memory 602, and computing devices 604. The memory 602 can be either random access memory or an EPROM such that the code stored within the memory 602 can be updated. The room light 100 may also include drivers 606 for the light projection areas 104. The drivers 606 can be either separate devices or can be software or firmware code included within the computing device 604 or the memory 602. Hardware, software, or a combination of hardware and software can control the various aspects of the room light 100.

The room light 100 is connected to a personal computer 112 that has an associated display 114. The connection between the room light 100 and the personal computer 112 can be either a direct connection or a connection through a network or similar architecture such as an IEEE 1394 interface. In one embodiment, the personal computer is also connected to a navigation camera system 116. The navigation camera system has two CCD camera arrays 118, and 120, capable of detecting light either reflected or emitted from position sensors 124 on a tracking device 126. It may be desirable to incorporate more than two CCD camera arrays into the light 100 so that the minimum number of arrays will be able to maintain a line of sight to the tracking devices 126 at all times. The operation of these camera array navigation systems is well known and will not be described further. The light 100 may also include a video camera 122 capable of video optical scanning. One such system is disclosed in Augmented Reality in the Operating Theatre of the Future, Proceedings of the 4th International Conference on Medical Image Computing and Computer-Assisted Intervention (MICCAI) Spring 2001, Pages 1195-1196, the disclosure of which is incorporated by reference. Further a variety of well-known position-sensing devices 124 can be used as the position sensors 124. These include both active and passive or reflective optical sensors, magnetic sensors, sonic sensors or projectors, inertial sensors or combination systems. Multiple tracking devices 126 are typically used during a surgical procedure. These tracking devices can be attached or associated with the anatomy of the patient 108 or associated or integrated into tools or instruments 128 to be used during the procedure.

Figure 2:
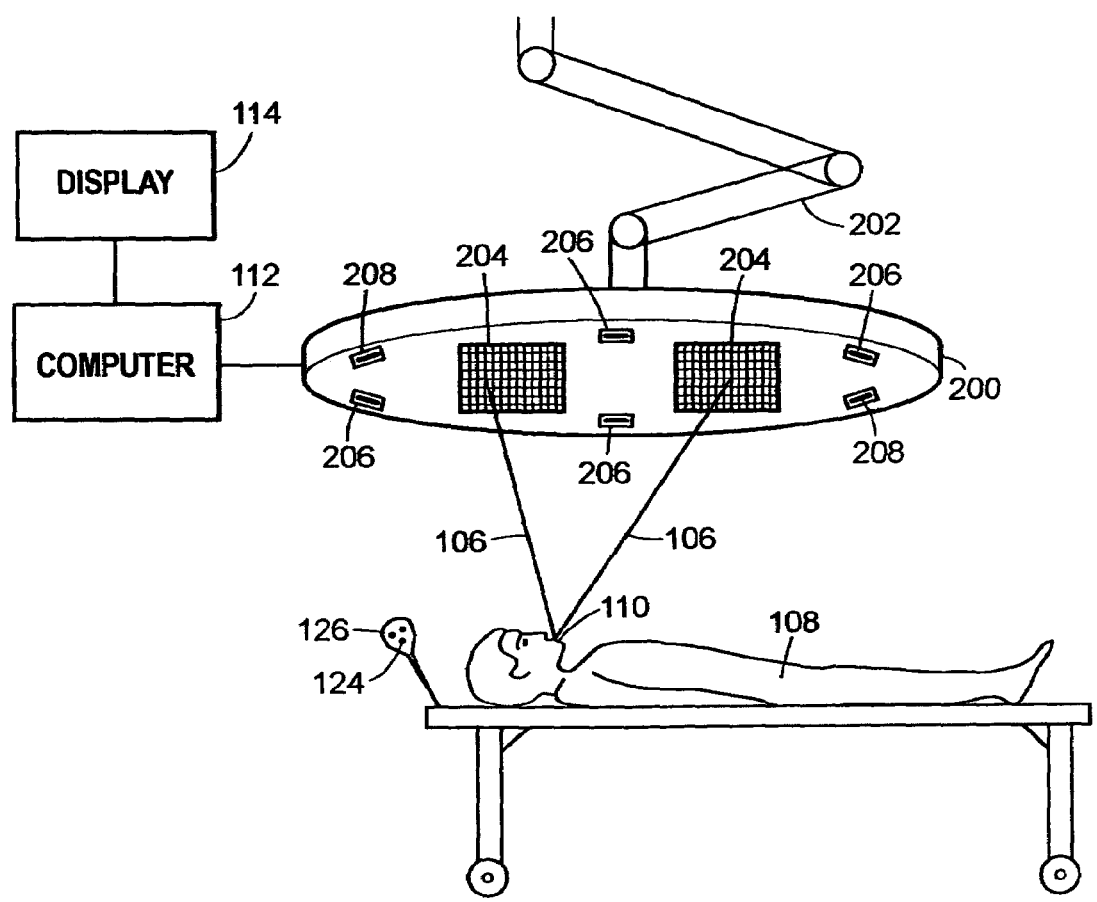
FIG. 2 is a schematic view of a second embodiment of the present invention.

FIG. 2 shows a further embodiment of the present invention. An operating room light 200 is suspended in position using a support system 202. The operating room light 200 includes light projection areas 204. These are similar to the light projection areas 104 described relative to FIG. 1. The operating room light 200 includes integrated locating cameras 206. FIG. 2 shows four locating cameras 206 spaced around the operating room light 200. Typically for optical systems, two cameras 206 are needed to determine the position of tracking devices 126 and instruments 128 with associated tracking devices 126. The use of added locating cameras 206 enables a sufficient number of localizing cameras 206 to be able to see the tracking devices 126 during a procedure without the need to readjust the operating room light 200. The operating room light 200 is connected to the personal computer 112 that has the associated display 114 in a manner similar to that described above either directly or through a network. In addition, a video camera 208 similar to that described above can also be incorporated in the operating room light 200.

The personal computer 112 can be any standard personal computer capable of using any of the operating systems available commercially. This includes Microsoft Windows, Apple OS and UNIX and similar operating systems. The computer 112 will have loaded software and drivers to enable the light projection areas 104 and 204 to both project sufficient light to illuminate the field of interest, such as a surgical field, and to display data light onto that same field of interest. The personal computer 112 will interact with the firmware and/or software within the room light 100 or the operating room light 200.

Figure 3:
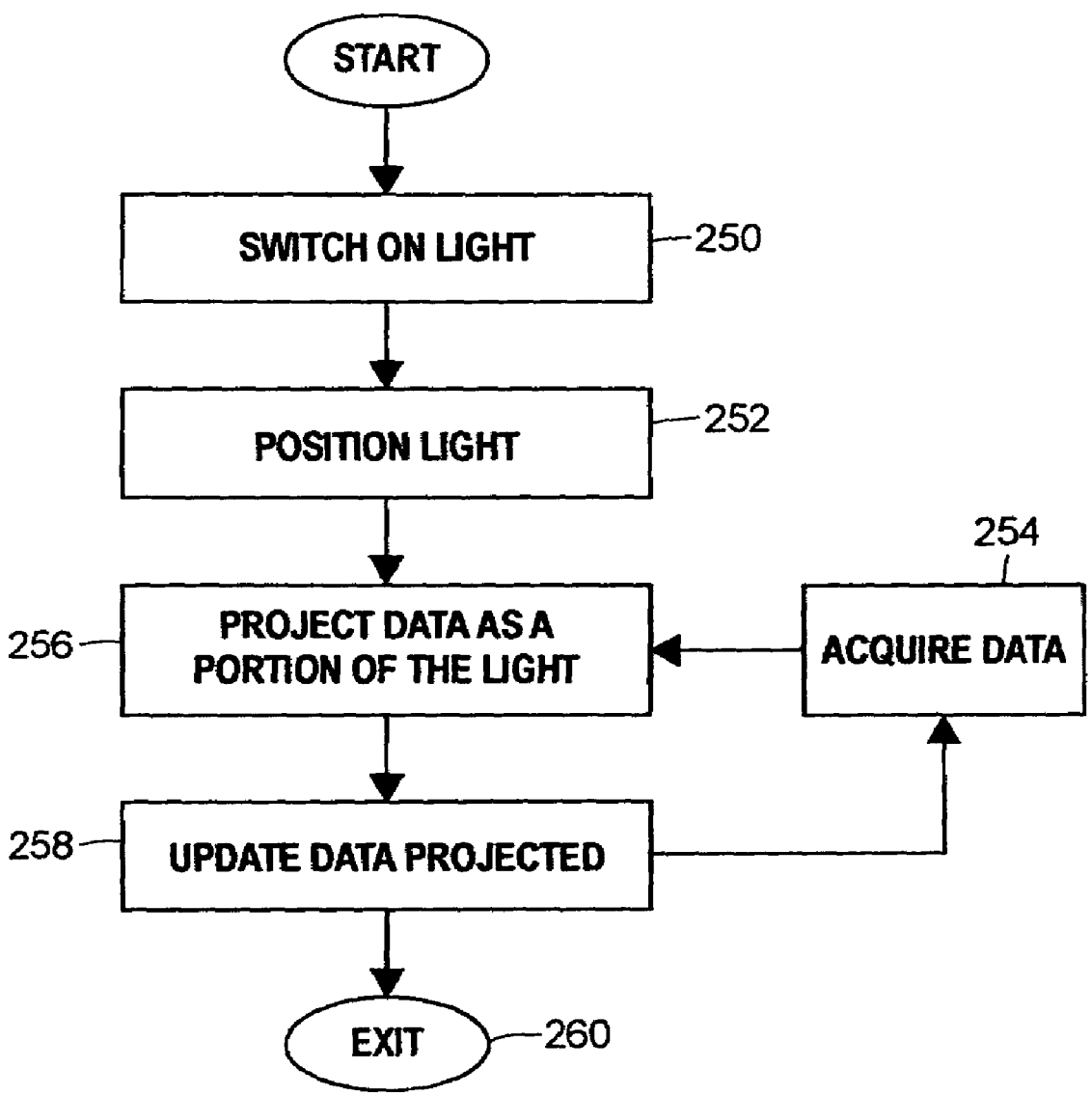
FIG. 3 is a flow diagram of one embodiment of the method of the present invention.

FIG. 3 shows a flow diagram of an embodiment of a method of the present invention. The method begins at a block 250 that instructs the system to switch on the light areas. A block 252 then enables the light to be positioned so that it projects sufficient light onto the field of interest. The order of the blocks 250 and 252 can be reversed and depending on the system used for the light, the block 252 can reposition the light elements during any procedure if needed. A block 254 acquires the data that is to be projected. The data can be acquired from a variety of sources including the navigation system, either one located internal to the operating room light 200 or external to the operating room light 200, external monitoring devices (not shown), the personal computer 112, other devices connected to the network, or any other source of data. The data acquired by the block 254 is passed to the system and instructs a block 256 to project data light elements along with the illumination light elements. Control then passes to a block 258 that determines if the projected data needs to be updated. If an update is needed control passes back to the block 254 that acquires the data and the loop continues to the block 256 to display the updated data. The sequence of the blocks 258, 254 and 256 will continue until the block 258 determines that the routine or process should be terminated. In this case, control passes to the exit 260.

Figure 4:
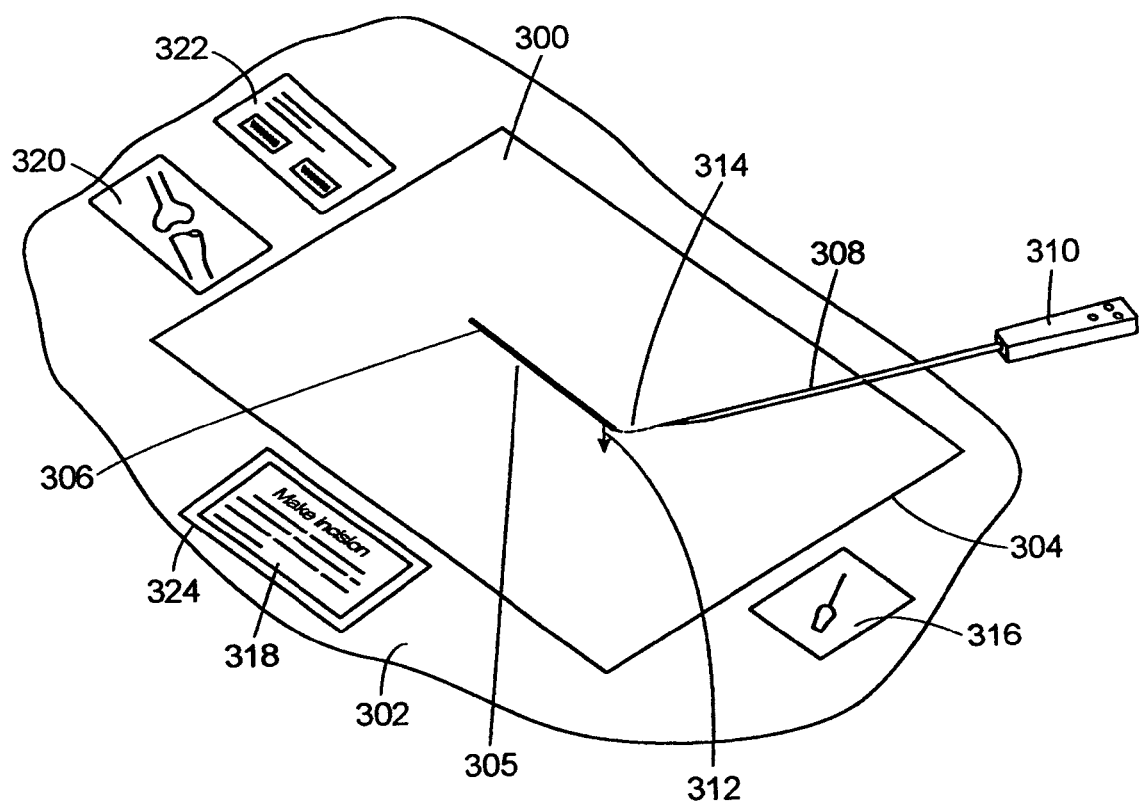
FIG. 4 is a schematic view of a surgical field showing the projection of data onto the field.

FIG. 4 illustrates how the data can be projected to a field of interest, in this case a surgical field 300. A surgical drape 302 covers a portion of the surgical field 300 and has an opening 304 to permit the surgical team to view a surgical site 305. Using the embodiment of FIG. 2, the operating room light 200 projects a line 306 onto the patient 108 within the surgical field 300. The line 306 indicates to the surgical team where to make the planned incision within the surgical site 305. A pointing device 308 or other device having a tracker 310 that is visible to the localizing cameras 206 is placed within the surgical field 300. The operating room light 200 projects an arrow 312 that indicates to the surgeon the direction the pointer 308 should be moved so that the pointer 308 is on a proper trajectory 314 as planned during the surgical pre-planning process. The preplanning process is part of the conventional use of surgical navigation systems and typically includes a pre-surgical scan using scanning technology such as a CT or an MRI scan. The surgeon will plan the surgical approach using the information obtained from these scans and this information is typically loaded into the personal computer 112 prior to beginning the surgical procedure. Alternatively, it is possible to develop this information intra-operatively using known procedures.

The operating room light may also be capable in various embodiments of projecting one or more of the following data elements either onto the surgical drape 302 surrounding the surgical site 305 or directly onto the surgical site 305 itself. Data view 316 shows the same view of the pointer 308 as displayed on the computer display 114. Data view 318 illustrates that a workflow checklist with various instructions to the team can also be projected. Alternatively, the data view 318 can include information that is updated or modified based on the presence, absence or position or a particular instrument within the surgical field 300. Data view 320 is a view of the anatomical structure to guide the surgeon to the proper positioning of the patient. Data view 322 shows a variety of vital signs that need to be monitored. These can be projected directly onto the field or the surrounding area to enable the surgical team to monitor the patient's vital signs without having to turn away to a separate monitor or display device. As indicated above, one or more of these data views can be projected In one embodiment, the surgical drape 302 can include reflective surfaces 324 to enhance the display of the projected light.

In a further embodiment, as the surgical site 305 is modified during the procedure by incisions, retractions, or other aspects of the surgical procedure, the system will self calibrate to enable the system to modify the data light projected so that the images are clear and undistorted.

Figure 5:
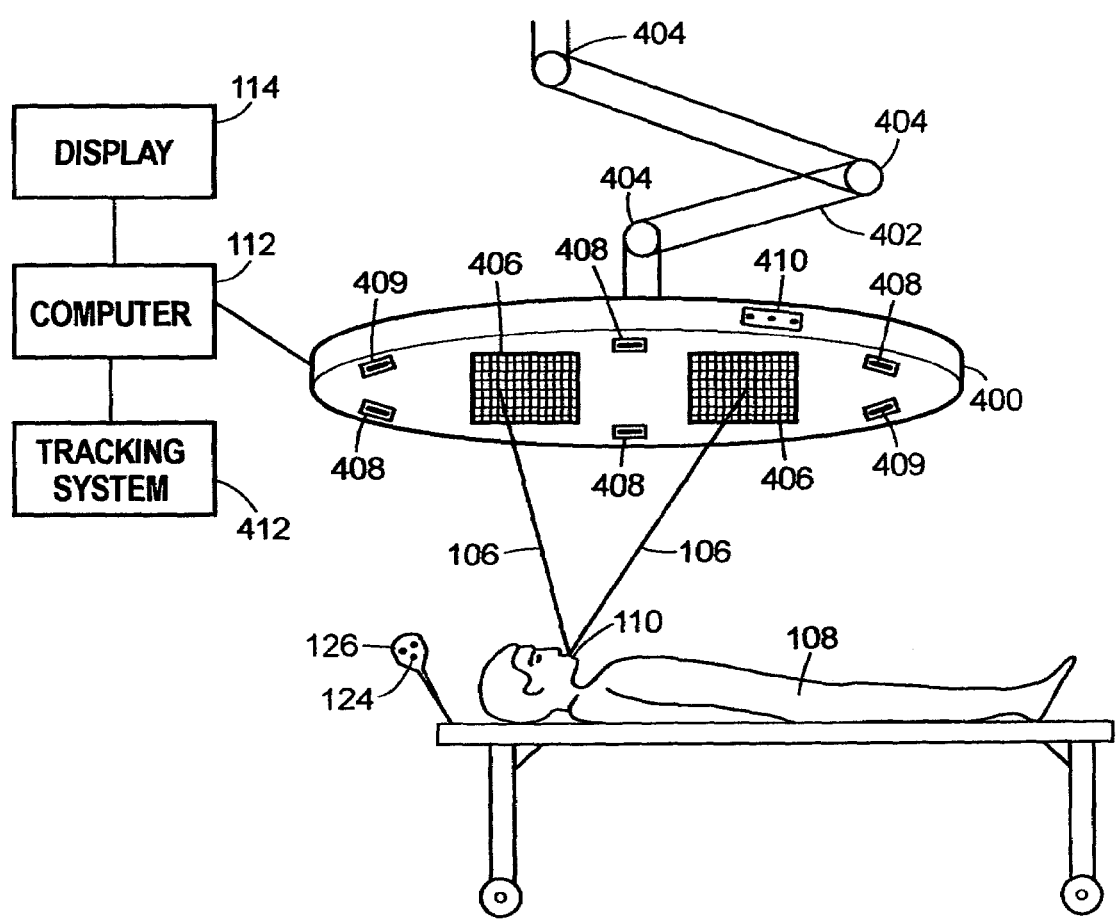
FIG. 5 is a schematic view of a third embodiment of the present invention.

FIG. 5 is a further embodiment of the present invention. An operating room light 400 has a support system 402 that has a series of motorized joints 404. The motorized joints 404 enable the support system 402 to position the operating room light 400 without the surgeon having to manually manipulate the operating room light 400. Furthermore, the motorized joints 404 enable a self-calibration process and the ability to automatically adjust the operating room light 400 to the best line of sight positions so that the operating room light 400 is in a position where the light rays shine perpendicularly (in average) on the patient's surface. The operating room light 400 has light projection areas 406, localizing cameras 408, and video cameras 409 similar to those described with reference to FIG. 2. Cameras 408 and 409 can be used for localization tasks and/or to assist the acquisition of surface scan data with photogrammetry techniques as described above. The operating room light 400 is also connected to the computer having the display in the same manner as above. The operating room light 400 may also include a tracking device 410 that can be tracked by an external tracking system 412 that is similar to the internal tracking system described previously. The combination of the motorized joints 404 and the external tracking system 412 can enable the system to automatically adjust the operating room light 400 to maintain the optimum projection angles for data projection.

Figure 6A:
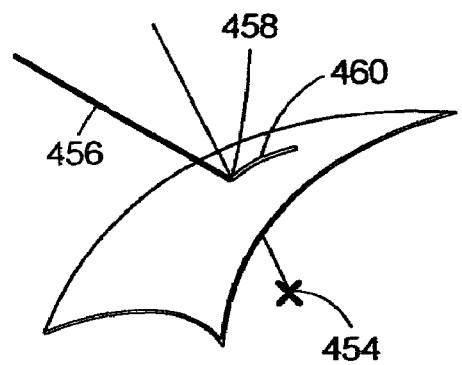
FIGS. 6a-e are a schematic representation of one embodiment of data light of the present invention
Figure 6B:
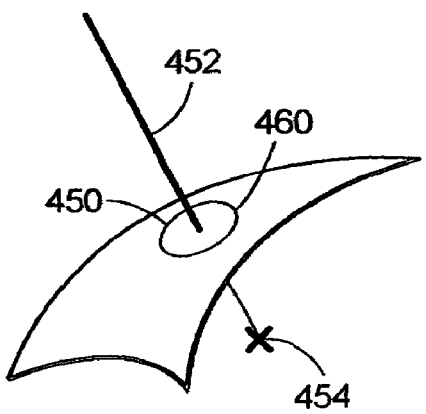
Figure 6C:
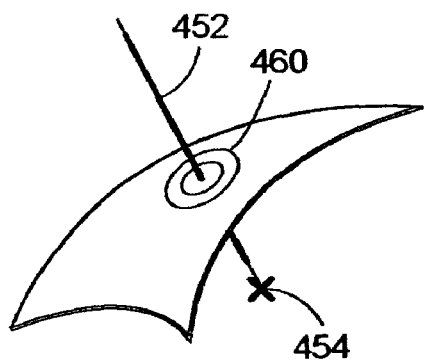
Figure 6D:
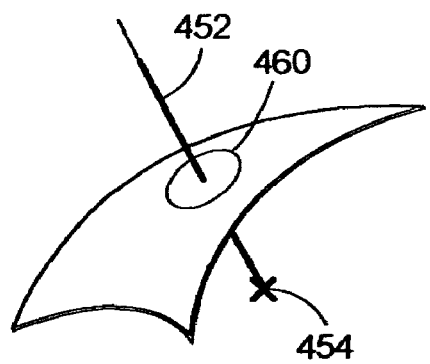
Figure 6E:
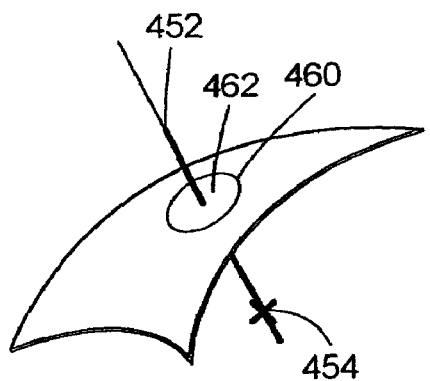

FIGS. 6a-e illustrate another embodiment of a data light 450 projected onto the patient. In FIGS. 6a-e, a planned trajectory 452 and a planned target point 454 are shown. An instrument 456 is moved toward an incision point 458 in FIG. 6a. Because the instrument is pointing at the incision point 458 that was located during the preplanning process or otherwise, but the trajectory of the instrument 456 does not match the planned trajectory, a line 460 is projected from the incision point 458. The direction and length of the line 460 indicates to the surgeon the direction to move the instrument 456. When the instrument 456 is at the proper point and on the proper trajectory as illustrated in FIG. 6b, the line disappears and is replaced by a circle of light 462 having an outer ring 464. The outer ring 464 can be distinguished from the circle of light 462 in any manner such as by a difference in brightness or color. As shown in FIG. 6c, as the instrument 456 penetrates on the trajectory 452 toward the target point 454, the outer ring 464 moves toward the incision point 458. The outer ring 464 is moved toward the incision point 458 as the instrument proceeds toward the target point 452, the circle of light 462 changes character, either by brightness change, color change or some other change to indicate that the instrument 456 is at the proper depth as shown in FIG. 6d. If the instrument 456 pass by the target point 454 as shown in FIG. 6e, the circle of light changes to yet a different character to warn that the instrument 456 has passed the target point 454.

Figure 7A:
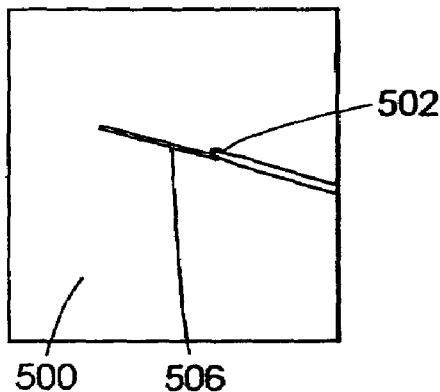
FIGS. 7a-e are a series of representations of the embodiment of FIGS. 6a-e.
Figure 7B:
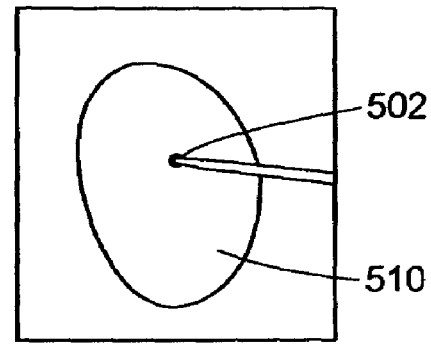
Figure 7C:
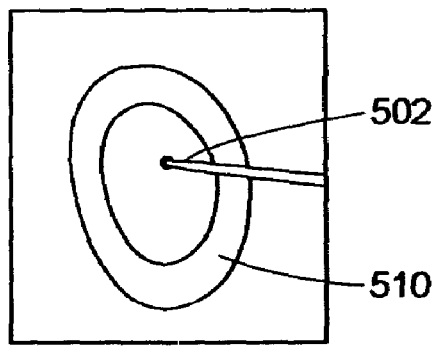
Figure 7D:
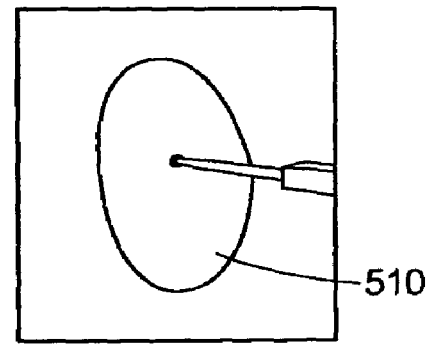
Figure 7E:
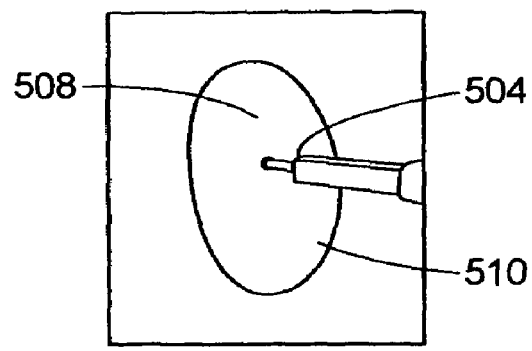

FIGS. 7a-e show views of light projected onto a simulated skin surface 500. FIGS. 7a-e correspond with the diagrammatic views of FIGS. 6a-e. In FIG. 7a, an instrument 502 is shown at an incision point 504. A line 506 indicates the direction and amount of adjustment of the trajectory of the instrument 502 necessary to place the instrument 502 on the planned trajectory line 452. FIG. 7b shows a circle of light 508 having an outer ring 510 as the instrument 502 is at the incision point 504 and on the proper trajectory 452. FIG. 7c shows the movement of the outer ring 510 toward the incision point 504 as the instrument 502 penetrates toward the target point 454. FIG. 7d shows the circle of light 508 with the change of character as the instrument 502 has reached the target point 454. FIG. 7e shows the change of character of the circle of light 508 as the instrument 502 passes by the target point 454. Other combinations of light that can perform the same functions as described above can be used.

Figure 8:
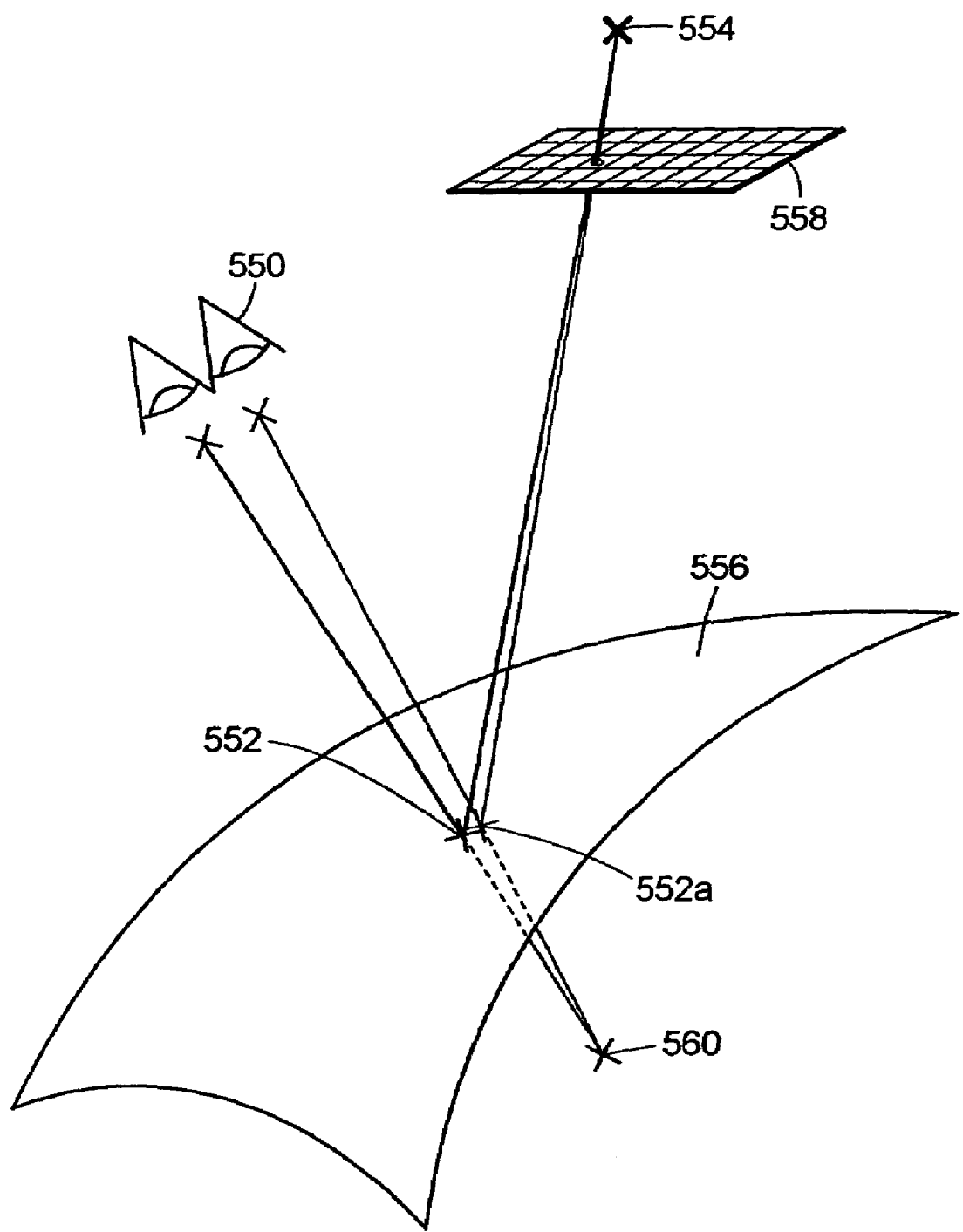
FIG. 8 is a schematic representation of a further embodiment of the present invention.

It is also possible to project a three dimensional image using polarized or colored lights using conventional three dimensional projection methodologies. FIG. 8 illustrates how a user 550 will see a three dimensional projection 552 and 552a of an image 554 of the letter "X" onto a surface 556 from a light source 558. The image 554 will appear to the user 550 as if the image 554 was at the target point 560.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications that come within the scope of the appended claims are reserved.

We claim:

1. A light source to illuminate a field of interest comprising:
   an illumination module that projects illumination light to the field of interest;
   a light projector that projects data light and is associated with the illumination module; and
   an input device associated with the light projector; wherein the input device sends signals to the light projector and the illumination module that cause the light projector simultaneously to project data light comprising surgical procedure information along with the illumination light to the field of interest; and
   wherein the illumination light comprises adequate ambient illumination light for viewing the field of interest during a procedure, and the data light is brighter than the ambient illumination light.

2. The light source of claim 1 where the data light displays the location of an instrument relative to a point within the field of interest.

3. The light source of claim 1 wherein the field of interest is a surgical field, and the data light displays pre-operative surgical procedure plan information and intra-operative tool guidance information on the field of interest.

4. The light source of claim 3 that includes a camera system to determine the location of an object within the surgical field.

5. The light source of claim 3 that includes a surface scanning module.

6. The light source of claim 5 wherein the surface scanning module includes a camera system to facilitate video optical scanning and localization of objects based on the scan information.

7. The light source of claim 5 that includes at least one video camera to facilitate video-optical scanning.

8. The light source of claim 4 where the camera system can detect infrared light from markers placed within the surgical field.

9. The light source of claim 8 where the markers emit infrared light.

10. The light source of claim 8 where the markers reflect infrared light.

11. The light source of claim 3 where the data light displays a surgical target.

12. The light source of claim 11 where the surgical target was determined pre-operatively from a pre-operative scan.

13. The light source of claim 3 where the data light displays a surgical approach.

14. The light source of claim 13 where the data light displays information about the location of an instrument relative to the surgical approach.

15. The light source of claim 3 where the data light displays anatomical structures.

16. The light source of claim 3 where the data light displays physiological data.

17. The light source of claim 16 where the physiological data includes at least one of blood flow, blood pressure, electrical fields, metabolism, electrolyte levels respiration rate, pulse rate, or temperature.

18. The light source of claim 3 where the data light displays physiological activity.

19. The light source of claim 3 where the data light displays information relating to life support systems and parameters.

20. The light source of claim 3 where the data light displays the progress of the surgical procedure.

21. The light source of claim 3 where the data light displays the data relative to attainment of a surgical goal.

22. The light source of claim 3 where the data light displays reference information.

23. The light source of claim 3 where the data light automatically updates the displays based on the position of the instrument within the surgical field.

24. The light source of claim 1 where the data light is displayed using digital light projection.

25. The light source of claim 3 where the data light displays data from a surgical navigation system.

26. The light source of claim 3 where the data light displays information specific to a particular surgical instrument being used.

27. The light source of claim 1 where the data light displays information in a three dimensional form.

28. The light source of claim 1 where the light projector comprises a matrix of light projection devices.

29. The light source of claim 28 where the light projector is capable of projecting colored light.

30. The light source of claim 1 that includes an adjustable support structure.

31. The light source of claim 30 where the support structure is remotely controlled.

32. The light source of claim 30 where the support structure is adapted automatically to achieve best line of sight or perpendicular light projection rays.

33. The light source of claim 1 wherein the data light is projected directly onto a surgical field.

34. The light source of claim 1 wherein the data light is projected onto a reflective surface within a surgical field.

35. The light source of claim 1 wherein visual information delivered by the data light is manipulated to conform to the shape of the surface onto which the visual information is projected.

36. The light source of claim 35 wherein the visual information is manipulated to conform to changes made to the surface onto which the visual information is projected.

37. The light source of claim 35 wherein the data light is calibrated by stereophotogrammetry using a calibration pattern.

38. The light source of claim 1 where the input device is a computer.

39. The light source of claim 38 where the computer is connected to a network.

40. The light source of claim 1 where the light source has control code and the code is upgradeable.

41. A light source to illuminate a field of interest comprising:
an illumination module comprising a series of digital light projectors, wherein at least a first of the digital light projectors projects ambient illumination light to the field of interest adequate for viewing the field of interest during a procedure and at least a second of the digital light projector is capable of projecting data light; and an input device associated with the illumination module;
wherein the input device sends signals to the illumination module that cause the first and second digital light projectors of the illumination module simultaneously to project data light along with the illumination light to the field of interest, and wherein the data light shows procedure plan information and instrument guidance information for conformance with the procedure plan.

42. The light source of claim 41 where the field of interest is a surgical field.

43. The light source of claim 42 that includes a camera system to determine the location of an object within the surgical field.

44. The light source of claim 42 where the data light displays a marker to identify a surgical target according to the procedure plan information.

45. The light source of claim 43 where the data light displays data from a surgical navigation system.

46. The light source of claim 42 where the light projector comprises a matrix of light projection devices.

47. The light source of claim 41 where the data light displays information in a three dimensional form.

48. The light source of claim 41 wherein visual information delivered by the data light is manipulated to conform to the shape of the surface onto which the visual information is projected.

49. The light source of claim 48 wherein the visual information is manipulated to conform to changes made to the surface onto which the visual information is projected.

50. The light source of claim 48 wherein the data light is calibrated by stereophotogrammetry using a calibration pattern.

51. The light source of claim 41 further comprising means for automatically moving the light source in response to feedback acquired through a navigation system to optimize the line of sight or the projection of the light.

52. A method of providing light to a field of interest during a procedure comprising the steps of:
sending control signals from an input device to an illumination module and a light projection module to simultaneously produce illumination light and data;
projecting the illumination light from the illumination module onto the field of interest;

projecting the data onto the field of interest from the light projection module associated with the illumination module simultaneously with the illumination light;

wherein the data comprises surgical procedure information;

capturing surface data from within the field of interest; and indicating a direction to move an instrument during the procedure in the field of interest using the projected data.

53. The method of claim 52 that includes the step of registering the surface data to the data projected from the light projection module.

54. The method of claim 52 that includes the step of tracking the location of the surface data.

55. The method of claim 52 that includes the step of updating the projected data.

56. The method of claim 52 wherein the light projection module is integral with the illumination module.

57. The method of claim 52 wherein the field of interest is a surgical site.

58. The method of claim 57 that includes the steps of modifying the data projected based on detection of a surgical instrument.

59. The method of claim 52 that includes the step of automatically adjusting the illumination light and the data light to optimize the line of sight or the projection of the illumination light or the data light in response to tracking information received from an external tracking system during the procedure.

60. The method of claim 52 that includes the step of calibrating the data projection using stereophotogrammetry.

61. The method of claim 57, further comprising the step of projecting planned instrument trajectory information onto the field of interest using the projected data.

62. The method of claim 61, further comprising the step of projecting information that indicates whether an instrument has reached a planned target point in the field of interest using the projected data.

* * * * *